United States Patent [19]

Manker

[11] Patent Number: 4,880,953
[45] Date of Patent: Nov. 14, 1989

[54] METHOD OF RECHARGING A HEAT PACK BY MICROWAVE ENERGY

[75] Inventor: Charles F. Manker, Chicago, Ill.

[73] Assignee: Prism Technologies, Inc., Chicago, Ill.

[21] Appl. No.: 289,559

[22] Filed: Dec. 23, 1988

[51] Int. Cl.$^4$ ................................ H05B 6/64
[52] U.S. Cl. ...................... 219/10.55 M; 219/10.55 R; 126/263
[58] Field of Search ............... 126/263, 400, 204, 206; 128/403; 219/10.55 M, 10.55 R

[56] References Cited

U.S. PATENT DOCUMENTS

| | | | |
|---|---|---|---|
| 3,519,517 | 7/1970 | Dench | 219/10.55 M |
| 4,077,390 | 3/1978 | Stanley et al. | 126/263 |
| 4,336,435 | 6/1982 | Kashyap | 219/10.55 M |
| 4,572,158 | 2/1986 | Fiedler | 126/263 |

Primary Examiner—James C. Yeung
Attorney, Agent, or Firm—Leydig, Voit & Mayer

[57] ABSTRACT

The invention is in a method of recharging or regenerating a substantially solid spent heat pack of the type in which a super-coolable salt solution is confined within a flexible plastic pouch and converted to solid form with evolution of heat, by contacting the solid contents of said pack with a source of microwave energy sufficient to melt the solid to the liquid state, without thereby damaging said heat pack.

3 Claims, No Drawings

METHOD OF RECHARGING A HEAT PACK BY MICROWAVE ENERGY

BACKGROUND OF THE INVENTION

This invention relates to an improved, highly reliable heat pack which is capable of passing from the super-cooled aqueous salt solution phase to a crystalline substantially solid phase with the generation of heat, and to the method of the subsequent recharging or regeneration of the super-cooled solution by raising the temperature of the substantially solid contents of a spent heat pack by contacting the contents with a source of microwave energy to thereby melt the solid to the liquid phase.

Heat packs which utilize a super-coolable aqueous salt solution that can be activated to liberate heat have become increasingly popular in recent years. Such heat packs as those shown in U.S. Pat. Nos. 4,077,390 and 4,572,158 and others, have significant advantages over former means of providing localized heat such as a hot water bottle or a heated electric element because of their portability and performance on short notice without the need for a supply of hot water or electricity to generate the heat. A super-cooled heat pack in its liquid state can be transported readily and is available on short notice to provide localized heat, as for the relief of pain and soreness in parts of the human body, as well as to warm parts of the body that have been subjected to extreme cold. Heat packs of this type are particularly useful in hospitals, clinics and in the home for the convenient generation of localized heat.

Up to now, it has always been necessary to place the spent substantially solid heat pack in a source of hot water and hold it there for a sufficient length of time and at a sufficiently high temperature of the water to melt the solid and return the contents of the heat pack to the liquid state. When that function has been accomplished the heat pack is ready for and capable of being reused, and the process can be repeated any number of times. Many users of such heat packs find the process of regeneration by immersion in hot water as described above to be inconvenient because of the time, appliances and care required to regenerate the pack without burning it. The result is that too often the discharged heat pack is set aside in the crystalline or solid state and is therefore useless for the quick application of localized heat since the user must first follow a lengthy process to regenerate or melt the contents in order to make it usable.

The foregoing disadvantage of heat packs known and used up until the present invention is a particular disadvantage in a hospital or clinic, particularly with the larger packs, where it becomes necessary to resort to the expense and use of the valuable time of hospital personnel to regenerate the spent heat packs to make them ready for reuse. As a result of this disadvantage, sales to this market have been significantly curtailed.

Flexible plastic heat packs of the type referred to above are shown in such U.S. patents as U.S. Pat. Nos. 4,379,448 and 4,460,546. The heat packs shown in these patents are unsatisfactory for microwave regeneration because such packs are known to contain internal welds which cause confined spaces within the pack resulting in hot spotting and melting or weakening of the flexible plastic pouch which thereby renders the heat pack unusable. In fact, such heat packs actually have carried a warning notice that the contents should not be microwaved to recharge or regenerate them.

SUMMARY OF THE INVENTION

It is a principal object and contribution of this invention to provide a method for recharging a spent heat pack by the application of microwave energy to the substantially solid contents to raise the temperature of the contents to the point at which the contents changes from the substantially solid phase to the liquid phase. In accordance with this invention heat packs are constructed so as to be devoid of internal welds which can define confined spaces and thereby impede the free transfer of heat within the melting solid or partially liquid contents during the time of microwave regeneration. Thus, the practice of the method of this invention results in the rapid reconversion of the contents of the heat pack from the solid to the liquid state without the danger of hot spotting or weakening or melting the plastic pouch during the process.

With this improvement, and following the method of this invention, heat packs treated according to the inventive process are regenerable in a matter of a few minutes in a standard microwave oven of the type found today in hospitals, clinics and in many homes.

As noted above, it is important for the successful use of the inventive process that the interior of the flexible plastic pouch should be devoid of spaces which significantly confine the movement of solution within the pack, as of the type that will be found when internal welds have been formed between the opposing flexible sides of the pouch and when the metallic activator employed in such heat packs becomes confined adjacent to such a welded junction between two surfaces, so that liquid or solid contents at such confined areas becomes overheated due to inadequate or too slow transfer of heat through the melting body of solid and liquid. If there were not certain clear advantages to having welds within the perimeter of the larger packs to provide a more equal distribution of solution, the ideal embodiment would be to have no internal welds.

DETAILED DESCRIPTION OF THE INVENTION

Prior to this invention it was a well recognized concept that the user of a heat pack should avoid bringing the heat pack into contact with a source of microwave energy because of the danger of local overheating and rupture of the heat pack. As noted above it was common practice in the trade to put a warning notice, either on the package itself or in the package literature, to avoid contact with microwave energy. And indeed, if one subjects a heat pack of the type described in the prior art mentioned above to a source of a microwave energy, the heat pack is subjected to hot spotting with resultant melting or weakening of the flexible plastic pouch and ultimate rupture with leaking of the contents.

I have now found that by constructing a sealed flexible plastic pouch in such a way that it is devoid of internal welds, which significantly restrict the flow of solution or entrap solution, and allowing the metallic activator to float freely in the body of material within the plastic pouch, I thereby allow for and do not impede the free transfer of heat within the melting solid contents of a heat pack until substantially the entire contents has passed into the liquid state. The source of microwave energy is then shut off before the contents has an opportunity to overheat and cause damage to the flexible plastic pouch. On the other hand, if the metallic activator is confined so that it cannot float freely in the contents, or if internal welds bring the opposing sides of the heat pack together to form a narrow passageway for the flow of liquid, the possibility for hot spotting and generation of excessive heat at the edges of the metallic activator or at the confined narrow passageways is aggravated with the resulting destruction of the heat pack.

In a preferred embodiment of the method one can manually or by timer intermittently start and stop the flow of microwave energy for short periods, as by intermittent pulses, to assure the free transfer of heat within the melting solid contents of the heat pack and thus avoid dangerous overheating. Alternatively, and in one preferred embodiment, the heat pack may be subjected to microwave energy for a short period of time, the energy shut off and the heat pack manually shaken or flexed to assist in transferring heat within the contents of the pack, and thereafter repeating the heating and flexing steps until the pack is recharged.

Following the inventive methods set forth herein and applying it to the heat pack of the type described herein results in a very significant advantage to the user of regenerable heat packs. In such places as hospitals and clinics, and in the home, it is no longer necessary to bother with boiling water and subjecting the spent heat pack to from 10 to 20 minutes of heating in order to regenerate it. Instead, the pack is placed dry inside a microwave oven of the usual type e.g., having an energy level between about 450 and 750 watts and simply subjecting it to the microwave energy under the conditions described herein until it is substantially in liquid form again and ready for reuse.

It will be apparent to those skilled in the art that various changes may be made in the method disclosed herein and in the construction and form of the heat packs disclosed herein without departing from the spirit and scope of this invention. The specific directions and forms given herein are presented for the purpose of making an understandable disclosure of the invention are not intended to be any restriction on the scope thereof, other than defined in the accompanying claims. It should be understood that I have explained a theory herein as to why microwave energy was never used before my invention and why I believe it is now possible to do so. Whether this theory is correct is not important to the actual invention; it being sufficient that my method works regardless of what theoretical explanation is used.

I claim as my invention:

1. In the method of recharging a flexible plastic pouch heat pack characterized by a sealed flexible plastic pouch which contains a supercoolable aqueous salt solution in its substantially crystallized solid form and a free-floating metallic activator for initiating crystallization, said pouch having no internal welds between opposing sides of said pouch which define confined spaces that are capable of significantly impeding movement of said activator or the movement of solution within the pouch when the solution is in at least partially liquid form thereby impeding the transfer of heat within the liquid and melting solid during recharging, the step of contacting said pack with a source of microwave energy sufficient to raise the temperature of said solution to the point at which it changes from a substantially solid phase to a liquid phase.

2. The method of claim 1 with the added provision of positioning the free floating activator so that it is not adjacent to a welded juncture between opposing sides of the flexible pouch.

3. The method of claim 1 wherein the microwave energy is supplied in intermittent pulses.

* * * * *